US00PP33443P3

(12) United States Plant Patent
Kordes

(10) Patent No.: US PP33,443 P3
(45) Date of Patent: Sep. 7, 2021

(54) FLORIBUNDA ROSE PLANT NAMED 'KORTANGWAL'

(50) Latin Name: *Rosa hybrida*
Varietal Denomination: KORtangwal

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/944,243

(22) Filed: Jul. 31, 2020

(65) Prior Publication Data

US 2021/0153404 P1 May 20, 2021

(30) Foreign Application Priority Data

Nov. 14, 2019 (AU) ..... PBR 2019/248

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141
CPC ..... A01H 6/749
See application file for complete search history.

(56) References Cited

U.S. PATENT DOCUMENTS

PP23,555 P2 4/2013 Kordes

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of floribunda rose plant, referred to by its cultivar name, 'KORtangwal', is described. The new variety forms in abundance on a substantially continuous basis attractive, light purple colored blossoms. The vegetation is vigorous, and the growth habit is very upright and bushy. Attractive glossy, dark green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORtangwal'.

CROSS-REFERENCE TO RELATED APPLICATIONS

This application claims priority to Australia Plant Breeders' Right Application Number 2019/248, which was filed on Nov. 14, 2019, the contents of which are hereby incorporated by reference for all purposes.

BACKGROUND OF THE INVENTION

The new variety of floribunda rose plant of the present invention was created by controlled breeding in May 2005 in Sparrishoop, Germany by artificial pollination wherein two parents were crossed which previously had been studied in the hope that they would contribute the desired characteristics. The female parent (i.e., the seed parent) was a seedling (non-patented) from a cross of 'KORpeligo' (non-patented) x unnamed seedling. The male parent (i.e., the pollen parent) of the new variety was 'KORchiaki' (non-patented).

The parentage of the new variety can be summarized as follows:

('KORpeligo' x unnamed seedling) x 'KORchiaki'

The seeds resulting from the above pollination were sown and small plants were obtained which were physically and biologically different from each other. Selective study resulted in the identification of a single plant of the new variety.

The new variety has been found to undergo asexual propagation at Wasco, Calif. and Cochranville, Pa. by a number of routes such as vegetative cuttings. Asexual propagation techniques in Wasco, Calif. and Cochranville, Pa., such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) abundantly and substantially continuously forms attractive, light purple colored blossoms,
(b) exhibits a very upright and bushy growth habit,
(c) forms vigorous vegetation, and
(d) forms attractive ornamental glossy, dark green foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed seedling seed parent originating from the ('KORpeligo' x unnamed seedling) cross displays a different flower shape and more disease resistance compared to the new variety. Additionally, the 'KORchiaki' (i.e., the pollen parent) displays more petals per flower and a lower level of disease resistance compared to the new variety. Moreover, the new variety can be readily distinguished from non-parental related similar varieties. For example, 'KORfriedhar' (U.S. Plant Pat. No. 23,555) displays more petals and buds that are less rounded in shape compared to the new variety.

The new variety has been named the 'KORtangwal' variety.

The first sale of the new variety was on September 2019 in Australia by the inventor or by another who obtained the new variety directly or indirectly from the inventor.

BRIEF DESCRIPTION OF THE PHOTOGRAPH

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a three-gallon container on its own roots at Cochranville, Pa., U.S.A. in June 2020.

The drawing sheet illustrates a specimen of the plant displaying flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on a two-year-old specimen of the new variety, observed during June, while growing on its own roots in a three-gallon container in Cochranville, Pa.

Botanical classification: *Rosa hybrida* cultivar KORtangwal.

Plant:

*Height*.—Approximately up to 60.0 cm from the top of the soil plane.

*Width*.—Approximately up to 50.0 cm.

*Habit*.—Very upright and bushy.

Branches:

*Stem color*.—Old wood: commonly near Yellow-Green Group 146A. young stems: commonly near Yellow-Green Group 144A.

*Length*.—Main stems: approximately 43.0 cm on average. — secondary stems: approximately 8.0 cm on average.

*Diameter*.—Main stems: approximately 6.0 mm on average. — secondary stems: approximately 3.0 mm on average.

*Thorns*.—Amount: moderate on lower ⅔ of the plant with one to two thorns per internode; very sparse on the upper ⅓ of the stems with one to zero thorns. — young thorns: length is approximately 5.0 mm on average; width is approximately 4.0 mm at point of attachment; color is commonly near Orange-Red Group 35C. — old thorns: length is approximately 5.0 m on average, width is approximately 3.0 mm at point of attachment; color is commonly near Red Group 42B.

Leaflets:

*Number*.—3, 5, and 7.

*Shape*.—Ovate; apex shape is acute to acuminate; and base shape is rounded.

*Margin*.—Serrate.

*Undulation*.—Moderate.

*Texture*.—Upper surface: smooth. — under surface: smooth.

*Size*.—Terminal leaflet: length is approximately 6.5 cm on average; width is approximately 4.0 cm on average. — lower leaflets: length is approximately 5.0 cm on average; width is approximately 3.0 cm on average. — 5-Leaflet leaf: length is approximately 16.0 cm on average; width is approximately 13.0 cm on average.

Foliage:

*Young foliage*.—Upper surface color: commonly near Greyed-Purple Group 187A with indistinguishable venation. — under surface color: commonly near Greyed-Purple Group 183B with indistinguishable venation.

*Old foliage*.—Upper surface color: commonly near Green Group NN137AA with indistinguishable venation. — under surface color: commonly near Green Group 137C with venation of near Green Group 138B.

*Petiole*.—Texture: upper surface is smooth; under surface is smooth. — length: approximately 4.0 cm on average. — diameter: approximately 1.0 mm on average. — upper surface color: commonly near Green Group NN137C. — under surface color: commonly near Yellow-Green Group 144A.

*Rachis*.—Upper surface color: commonly near Green Group NN137C. — under surface color: commonly near Yellow-Green Group 144A. — length: approximately 10.0 cm on average. — diameter: approximately 1.0 mm on average.

*Stipules*.—Length: approximately 2.0 cm on average. — width: approximately 5.0 mm on average. — margin: Entire to erose. — upper surface color: commonly near Yellow-Green Group 144A with the majority of the innermost portion near Greyed-Purple Group 184B. — lower surface color: commonly near Yellow-Green Group 144A.

Inflorescence:

*Number of flowers*.—About 16 blooms on average on a plant at once.

*Number of blossoms per stem or in a cluster*.—Typically, between 3 and 6 blooms per stem cluster on average.

*Blooming season*.—Typically, in bloom from June to November in Southeastern Pennsylvania.

*Peduncle*.—Color: commonly near Yellow-Green Group 144A. — diameter: approximately 3.0 mm on average. — length: approximately 2.0 cm on average. — surface texture: smooth.

*Sepals*.—Number 5. — upper surface color and texture: commonly near Yellow-Green Group 144A, covered in short pubescence. — under surface color and texture: commonly near Yellow-Green Group 144B; puberulent. — size: length is approximately 2.0 cm on average; width is approximately 1.0 cm on average. — margin: entire with extension on two or three sepals measuring 5.0 mm in length and 1.0 mm in width. — apex: acute to aristate. — base: truncate as it joins the receptacle.

*Buds*.—Shape: globular. — size: length is approximately 1.0 cm on average; width is approximately 1.3 cm on average. — color (when opening): commonly near Red-Purple Group 68A.

*Flower*.—Form: double, cuplike. — profile: flat. — diameter: approximately 7.0 cm on average. — height: approximately 3.0 cm on average. — duration: on the plant approximately 7 days. — petal color when first and fully opened: upper surface is commonly near Purple Group N76B with a small basal blotch near Red-Purple Group 69D; under surface is commonly near Purple Group 75C. — petal color at end of blooming: upper surface is commonly near Purple Group 75D; under surface is commonly near Purple Group 75B.

*Petaloids*.—Color: commonly near Purple Group N76B. — number: 5. — length: approximately 1.0 cm on average. — width: approximately 5.0 mm on average.

*Fragrance*.—Slight sweet scent.

*Petal*.—Number: 45 on average. — drop: good. — length: approximately 3.0 cm on average. — width: approximately 3.5 cm on average. — overall shape: broadly obovate. — margin: entire with mild undulation. — apex shape: rounded to slightly cuspidate. — base shape: Cuneate.

*Stamen*.—Number: approximately 120. — anthers: number is approximately 120; color is commonly near Yellow-Orange Group 16C; length is approximately 2.0 mm; shape is oval. — filaments: length is approximately 5.0 mm on average; color is commonly near Yellow Group 2B.

*Pistils*.—Arrangement: separate and free. — number: approximately 112. — style: length is approximately 3.0 mm; color is commonly near Red Group N45C. — stigma: color is commonly near Yellow Group 13B; diameter is less than 1.0 mm; shape is fan shaped.

*Receptacle*.—Size: 6.0 mm diameter. — depth: 5.0 mm. — shape: urn shaped. — color: commonly near Yellow-Green Group 144A. — surface texture: smooth.

*Pollen*.—Color: commonly near Yellow-Orange Group 23A. — amount: sparse.

*Hips/seed*.—None observed.

Development:

*Vegetation*.—Glossy, dark green, vigorous and strong.

*Blossoming*.—Abundant and substantially continuous from spring through frost.

*Resistance to diseases*.—Good resistance for powdery mildew (*Sphaerotheca pannosa*) and rust (*Phragmidium tuberculatum* and *Phragmidium mucronatum*).

*Hardiness*.—Hardy to USDA Zone 6b.

The new 'KORtangwal' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant characterized by the following combination of characteristics:

(a) abundantly and substantially continuously forms attractive, light purple colored blossoms, (b) exhibits a very upright and bushy growth habit, (c) forms vigorous vegetation, and (d) forms attractive ornamental glossy, dark green foliage; substantially as herein shown and described.

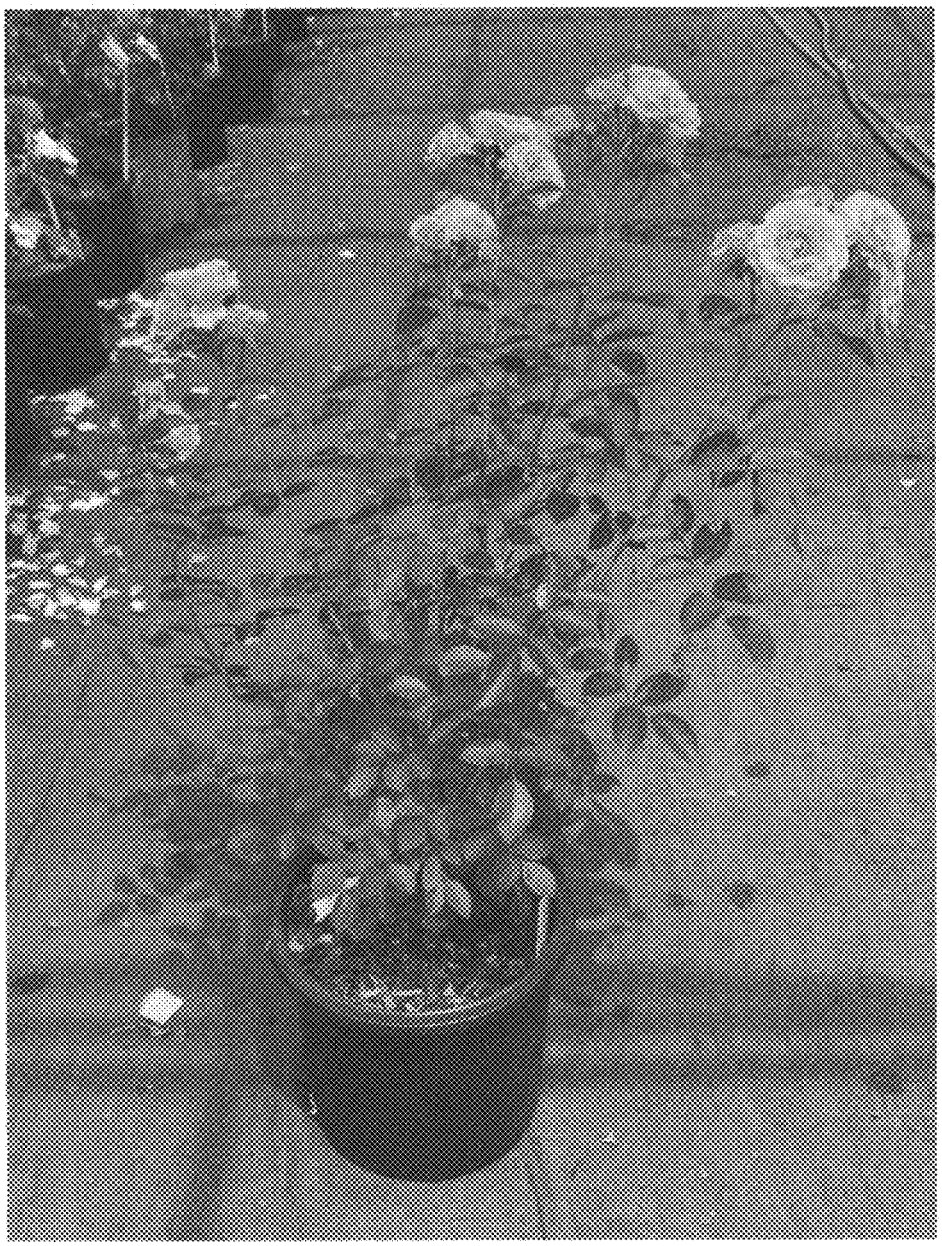

* * * * *